United States Patent [19]

Lal et al.

[11] Patent Number: 4,479,948
[45] Date of Patent: Oct. 30, 1984

[54] TRIAZINO(2,1-A)ISOQUINOLINE DERIVATIVES, COMPOSITIONS AND THEIR USE AS MEDICAMENTS

[75] Inventors: Bansi Lal, Mulund; Adolf D'Sa, Vikhroli; Alihussein N. Dohadwalla, Cumballa Hill; Noel J. de Souza, Santa Cruz, all of India; Horst Dornauer, Kelkheim, Fed. Rep. of Germany

[73] Assignee: Hoechst Aktiengesellschaft, Frankfurt am Main, Fed. Rep. of Germany

[21] Appl. No.: 396,393

[22] Filed: Jul. 8, 1982

[30] Foreign Application Priority Data

Jul. 8, 1981 [DE] Fed. Rep. of Germany ....... 3126837

[51] Int. Cl.$^3$ .................. A61K 31/53; A61K 31/535
[52] U.S. Cl. ............................ 424/248.4; 424/248.5; 424/248.55; 424/248.56; 424/248.57; 424/248.58; 424/249; 544/113; 544/211; 544/212
[58] Field of Search ............... 544/113, 208, 211, 212; 424/248.55, 248.4, 248.5, 248.56, 248.57, 248.58, 249

[56] References Cited

FOREIGN PATENT DOCUMENTS 10759 5/1980 European Pat. Off. .
1922837 11/1969 Fed. Rep. of Germany .
2801289 5/1979 Fed. Rep. of Germany .

OTHER PUBLICATIONS

Reimlinger, Chemical Abstracts, vol. 75 (1971), 140800j.

Primary Examiner—Robert W. Ramsuer
Attorney, Agent, or Firm—Curtis, Morris & Safford

[57] ABSTRACT

Hypotensively active triazino-(2,1-a)isoquinoline compounds having the ring system

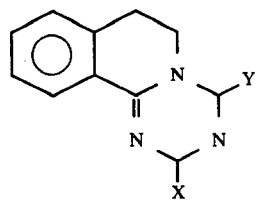

and methods of making and using such compounds.

12 Claims, No Drawings

TRIAZINO(2,1-A)ISOQUINOLINE DERIVATIVES, COMPOSITIONS AND THEIR USE AS MEDICAMENTS

The invention relates to a new class of triazino(2,1-a)isoquinoline derivatives and a process for the preparation of the compounds according to the invention. The triazino(2,1-a)isoquinoline derivatives of the present invention have valuable pharmacological properties, for example hypotensive properties, detectable in cats and dogs.

Thus the invention relates to triazino(2,1-a)isoquinoline derivatives having a new heterocyclic ring system of the formula I

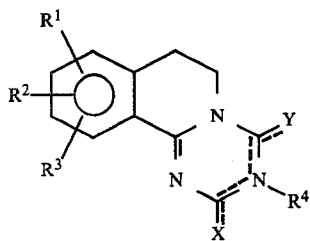

in which $R^1$, $R^2$ and $R^3$ can be identical or different and can be hydrogen, lower alkoxy, acyloxy or halogen, it being possible for two adjacent radicals $R^1$, $R^2$ and $R^3$ together to denote an alkylenedioxy group, preferably a methylenedioxy or ethylenedioxy group; $R^4$ denotes an electron pair, hydrogen or lower alkyl; X denotes halogen, an oxygen or sulfur atom, imino, which can be substituted by lower alkyl or aryl, alkylthio, alkoxy or $NR^5R^6$, in which $R^5$ and $R^6$ each can be hydrogen, lower alkoxy, amino, lower alkylamino, lower dialkylamino, acylamino, lower alkoxycarbonylamino, a nitrogen-containing heterocyclic radical, lower alkyl, $C_3$-$C_6$-cycloalkyl, lower dialkylaminoalkyl, aralkyl or lower alkyl which is substituted by a heterocycle, or aryl, or in which $R^5$ and $R^6$ together with the nitrogen atom to which they are bonded can be an optionally substituted nitrogen heterocycle which can contain a further nitrogen or oxygen atom, Y denotes an oxygen or sulfur atom, lower alkylthio or $NR^7R^8$, in which $R^7$ and $R^8$ have the meanings indicated for $R^5$ and $R^6$, and their acid addition salts.

In the above connection, "lower groups" are understood to be groups having 1 to 6 carbon atoms.

Preferred lower alkoxy groups for $R^1$, $R^2$, $R^3$, $R^5$, $R^6$, $R^7$ or $R^8$ are, for example, those having up to 3 carbon atoms.

Suitable acyloxy radicals for $R^1$, $R^2$ or $R^3$ are, for example, those in which the acyl group denotes a straight-chain or branched alkanoyl group having 1-6 carbon atoms, for example, the acetyl group, or an aroyl group, in particular the benzoyl group having a phenyl nucleus which is optionally substituted once to three times by halogen, nitro, hydroxyl, $C_1$-$C_3$-alkoxy and $C_1$-$C_3$-alkyl groups.

If $R^1$, $R^2$, $R^3$ or X denote a halogen atom, a preferred radical which may be mentioned is, for example, chlorine.

Suitable alkyl radicals for X, Y, $R^4$, $R^5$, $R^6$, $R^7$ or $R^8$ are those having a maximum of 6 carbon atoms, such as, for example, methyl, ethyl, n-propyl, isopropyl, isobutyl or tert.-butyl.

Suitable alkylamino or dialkylamino radicals for $R^5$, $R^6$, $R^7$ or $R^8$ are particularly those having alkyl groups having a maximum of 3 carbon atoms, for example methylamino or dimethylamino groups.

A particularly suitable acylamino radical for $R^5$, $R^6$, $R^7$ or $R^8$ is the ethoxycarbonylamino radical.

Suitable cycloalkyl radicals which may be mentioned for $R^5$, $R^6$, $R^7$ or $R^8$ are those having a maximum of 6 carbon atoms, such as, for example, cyclohexyl.

A suitable substituted alkyl radical for $R^5$, $R^6$, $R^7$ or $R^8$ is a radical having up to 6 carbon atoms which is substituted once or twice by di-($C_1$-$C_4$)-alkylamino groups.

Examples of aralkyl radicals for $R^5$, $R^6$, $R^7$ or $R^8$ are those having a maximum of 8 carbon atoms, in which the aryl radical can be a phenyl radical which is substituted once or more times, in particular a phenyl radical which is substituted once, twice or three times by halogen, nitro, hydroxyl, $C_1$-$C_3$-alkoxy or $C_1$-$C_3$-alkyl.

Examples of suitable nitrogen-containing heterocyclic radicals which may be mentioned are piperidino, morpholino or piperazino, which can be substituted by $C_1$-$C_3$-alkyl, aralkyl, $C_1$-$C_3$-alkoxy, aryl or nitrogen heterocycles having the meaning indicated above.

Suitable aryl radicals are unsubstituted phenyl radicals or phenyl radicals which are substituted once, twice, or three times by halogen, hydroxyl, nitro, $C_1$-$C_3$-alkoxy or $C_1$-$C_3$-alkyl.

Examples of salts of the triazino(2,1-a)isoquinoline derivatives according to the invention which may be mentioned are those of inorganic or organic acids, such as hydrochlorides, hydrobromides, sulfates, phosphates, acetates, oxalates, tartrates, citrates, maleates or fumarates.

Preferred substituents are:
for $R^1$ or $R^2$: $C_1$-$C_3$-alkoxy;
for $R^3$: hydrogen;
for $R^4$: an electron pair, hydrogen or $C_1$-$C_6$-alkyl;
for X: oxygen, a lower alkylimino or arylimino group or the group $NR^5R^6$, $R^5$ and $R^6$ preferably representing hydrogen, nitrogen-containing heterocyclic radicals, lower alkyl or aryl, and $R^5$ and $R^6$, together with the nitrogen atom to which they are bonded denoting an optionally substituted nitrogen heterocycle which can contain a further heteroatom;
for Y: oxygen, sulfur, alkylthio or the group $NR^7R^8$, $R^7$ and $R^8$ preferably denoting hydrogen, a nitrogen heterocycle, lower acylamino, lower alkyl or aryl or in which $R^7$ and $R^8$, together with the nitrogen atom to which they are bonded, denote an optionally substituted nitrogen heterocycle, which can contain a further heteroatom.

Particularly preferred compounds according to the present invention are:
9,10-dimethoxy-2-tert.-butylamino-6,7-dihydro-4H-triazino(2,1-a)isoquinolin-4-one hydrochloride,
9,10-dimethoxy-b 2-(2,4-dichloroanilino)-6,7-dihydro-4H-triazino(2,1-a)isoquinolin-4-one hydrochloride,
9,10-dimethoxy-2-mesitylamino-6,7-dihydro-4H-triazino(2,1-a)isoquinolin-4-one hydrochloride monohydrate,
9,10-dimethoxy-2-morpholino-6,7-dihydro-4H-triazino(2,1-a)isoquinolin-4-one hydrochloride,
9,10-dimethoxy-2-mesitylimino-4-(4-methylanilino)-6,7-dihydro-2H-triazino(2,1-a)isoquinolin hydriodide,
9,10-dimethoxy-2-mesitylimino-4-amino-6,7-dihydro-2H-triazino(2,1-a)isoquinoline hydriodide monohydrate and 9,10-dimethoxy-2-mesitylimino-4-(2,4-dimethylanilino)-6,7-dihydro-2H-triazino(2,1-a)isoquinoline hydriodide monohydrate.

Some new triazino(2,1-a)isoquinoline derivatives, together with their salts and melting points, are listed in the following table.

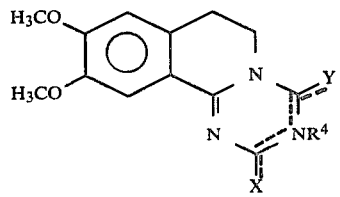

| R⁴ | X | Y | Salt | Melting point (°C.) |
|---|---|---|---|---|
| H | O | O | | 292–293 |
| : | NH₂ | O | — | 283–284 |
| : | NH—N(piperidinyl) | O | HCl.0.5H₂O | 275–278 |
| : | HN(CH₂)₃CH₃ | O | HCl.H₂O | 248–250 |
| : | HNCHMe₂ | O | HCl.H₂O | 228–231 |
| : | HNCH₂CHMe₂ | O | HCl.H₂O | 215–218 |
| : | HNCMe₃ | O | HCl | 243–245 |
| : | HN-(thiacyclohexyl S) | O | HCl | 238–239 |
| : | HN(CH₂)₃NMe₂ | O | 2HCl.H₂O | 238–241 |
| : | HN-(2,4-dichlorophenyl) | O | HCl | 222–224 |
| : | HN-(3,4-dimethoxyphenyl) | O | HCl | 270–271 |
| : | HN-(2,4-dimethylphenyl) | O | HCl | 222–224 |
| : | HN-(2,4,6-trimethylphenyl) | O | HCl.H₂O | 240–242 |
| : | N(azepanyl) | O | HCl | 255–256 |
| : | N(morpholinyl) | O | HCl | 252–253 |

-continued
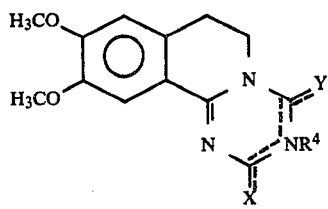
| R⁴ | X | Y | Salt | Melting point (°C.) |
|---|---|---|---|---|
| : | N⌒N—CH₃ (N-methylpiperazine) | O | HCl.0.5H₂O | 275–278 |
| : | NCHMe₂ | S | — | 253–254 |
| : | NCHMe₂ | SC₂H₅ | HI | 208–211 |
| : | NCHMe₂ | NH₂ | CH₃SO₃H.H₂O | 204–206 |
| : | NCHMe₂ | HN—CH₂—C₆H₅ | HI | 240–241 |
| : | NCHMe₂ | HN—CH₂—CH₂—C₆H₃(OCH₃)₂ | HI | 220–222 |
| : | NCHMe₂ | HNCH₂CHMe₂ | HI | 247–249 |
| : | NCHMe₂ | HN—(2,4-diMe-C₆H₃) | HI | 246–248 |
| : | NCHMe₂ | N⌒O (morpholine) | HI | 214–215 |
| : | N-(2,4,6-triMe-C₆H₂) | NH₂ | HI—H₂O | 261–263 |
| : | N-(2,4,6-triMe-cyclohexyl) | NH—NHCO₂Et | 0.5H₂O | 276–278 |
| : | N-(2,4,6-triMe-cyclohexyl) | HNCH₂CHMe₂ | CH₃SO₃H.2H₂O | 186–287 |

-continued

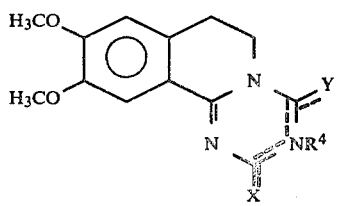

| $R^4$ | X | Y | Salt | Melting point (°C.) |
|---|---|---|---|---|
| : | CH₃ (2,4,6-trimethylphenyl-N) | HN(CH₂)₉CH₃ | CH₃SO₃H | 122–125 |
| : | CH₃ (2,4,6-trimethylphenyl-N) | HN—C₆H₄—CH₃ (p-tolyl) | HI | 258–260 |
| : | CH₃ (2,4,6-trimethylphenyl-N) | HN—C₆H₃(CH₃)₂ (2,4-dimethylphenyl) | HI.H₂O | 252–255 |
| : | CH₃ (2,4,6-trimethylphenyl-N) | HN—CH₂—CH₂—C₆H₃(OCH₃)₂ | CH₃SO₃H.2H₂O | 219–220 |
| : | CH₃ (2,4,6-trimethylphenyl-N) | HN—C₆H₂(OCH₃)₃ | CH₃SO₃H | 285–288 |

The present invention additionally relates to a process for the preparation of the triazino(2,1-a)isoquinoline derivatives according to the invention which comprises (a) preparing compounds of the formula I, in which $R^4$ is hydrogen and X and Y each denote oxygen, represented by the formula Ia

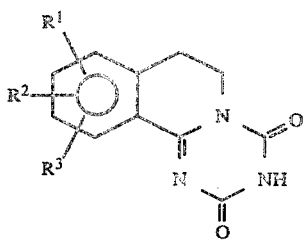

(Ia)

by reaction of a compound of the formula II

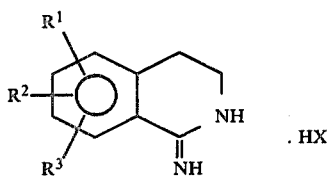

(II)

in which $R^1$, $R^2$ and $R^3$ have the meaning indicated above and X represents a halogen atom, for example, a chlorine, bromine or iodine atom, with a compound of the formula III

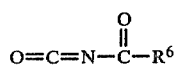

(III)

$$O=C=N-\overset{\overset{O}{\|}}{C}-R^6$$

in which $R^6$ denotes a removable protective group, such as, for example, ethoxy group, in the presence of a base, such as, for example, sodium hydride and a solvent, for example, an aromatic hydrocarbon, such as benzene at temperatures from room temperature up to the boiling point of the particular solvent, it being possible for the compounds of the formula II to be prepared by known processes (see S. African Pat. No. 6901, 552 (1969), cf. C.A. 72, 111309 p (1970); C.A. 58, 503 (1963); or (b) preparing compounds of the formula I, in which $R^4$ denotes an electron pair, X denotes the group $NR^5R^6$ and Y denotes an oxygen atom, represented by the formula Ib

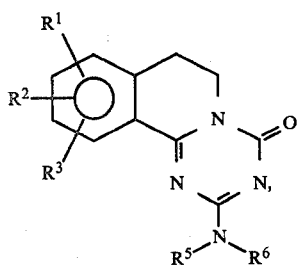

by reaction of compounds of the formula Ia with a halide such as, for example, phosphorus oxytrichloride, and subsequent reaction with compounds of the formula IV

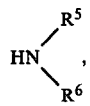 (IV)

in which $R^5$ and $R^6$ have the meaning indicated above, optionally in the presence of a base of an acid acceptor such as, for example, a compound of the formula

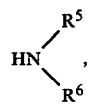

which is employed in excess, or an alkali metal hydride such as, for example, sodium hydride or a tertiary amine such as, for example, triethylamine or an acid acceptor such as, for example, diazabicyclononene, it being possible for the reaction to be carried out in the presence of a polar solvent, such as dimethylformamide or dimethyl sulfoxide, of halogenated hydrocarbons, such as chloroform, or of alkanols, such as butanol, of aprotic solvents, such as high-boiling ethers, for example diethylene glycol dimethyl ether, and it being possible to complete or accelerate the reaction by heating up to the boiling point of the particular solvent, or (c) preparing compounds of the formula I, in which $R^4$ denotes an electron pair, X denotes a group of the formula $NR^5R^6$, and Y denotes a sulphur atom, represented by the formula Ic

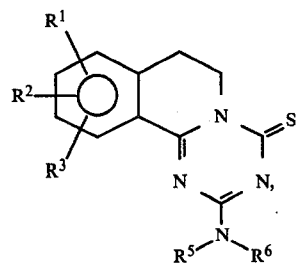

by reaction of a compound of the formula Ib with a sulfide, such as, for example, phosphorus pentasulfide or 2,4-bis-(4-methoxyphenyl)-1,3,2,4-dithiadiphosphetane-2,4-disulfide [S. Scheibye, B. S. Pederson and S. O. Lawesson, Bull. Soc. Chem. Belg. 87, 229 (1978)] in the presence of a solvent, for example an aromatic hydrocarbon, such as benzene or an aprotic polar solvent, such as, for example, hexamethylphosphoric triamide or dioxane, at a temperature of 50°–150° C., or (d) preparing compounds of the formula I, in which $R^4$ denotes an electron pair, X denotes a group of the formula $NR^5R^6$, in which $R^6$ is an electron pair, Y denotes SAlk and Alk denotes a $C_1$-$C_4$-alkyl group, such as ethyl, represented by the formula Id

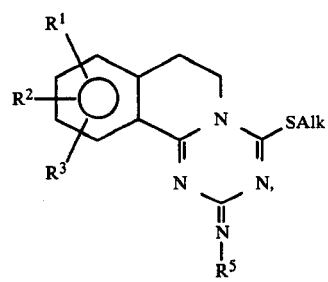

by reaction of a compound of the formula Ic, in which $R^6$ denotes hydrogen, with an alkyl halide, such as, for example, ethyl iodide, in the presence of a polar solvent, such as, for example, dimethylformamide, of halogenated hydrocarbons, such as, for example, chloroform or of an aprotic solvent, such as, for example tetrahydrofuran, it being possible for the reaction to be completed or accelerated by the application of heat, for example, by heating up to the boiling point of the particular solvent, or (e) preparing compounds of the formula I, in which $R^4$ denotes an electron pair, X denotes a group of the formula $NR^5R^6$, in which $R^6$ represents an electron pair, Y denotes a group of the formula

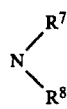

in which $R^7$ and $R^8$ have the meanings indicated above, represented by the formula Ie

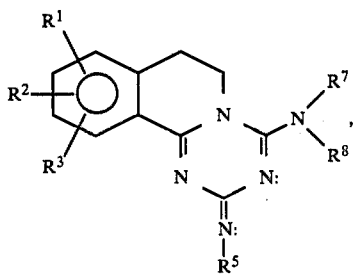

by reacting a compound of the formula Id with a compound of the formula V

in which $R^7$ and $R^8$ have the meanings given above, optionally in the presence of a base or an acid acceptor, for example a compound of the formula $NHR^7R^8$, which is employed in excess, or of an alkali metal hydride, such as, for example, sodium hydride, of a tertiary amine, such as, for example triethylamine, or of an acid acceptor, such as, for example, diazabicyclononene, it being possible for the reaction to be carried out in the presence of a polar solvent, such as, for example, dimethylformamide or dimethyl sulfoxide, of halogenated hydrocarbons, such as, for example, chloroform, of alkanols, such as, for example, butanol or of aprotic solvents, such as high-boiling ethers, for example, diethylene glycol dimethyl ether, and it being possible for the reaction to be completed or accelerated by heating up to the boiling point of the particular solvent.

The compound of the formula I obtained according to the invention can, if appropriate, be converted into its acid addition salt with one of the acids mentioned above as an example.

The triazino(2,1-a)isoquinoline derivatives according to the invention have hypotensive activity, as has been demonstrated by animal experiments on dogs and cats and thus they are suitable for the treatment of high blood pressure in human and veterinary medicine.

Because of the hypotensive activity, the new active substances are suitable for the treatment and prophylaxis of cardiovascular diseases, such as, for example, essential and malignant hypertension, cardiac insufficiency, angina pectoris and disturbances of the peripheral circulation. The active substances can also be employed in combination with other pharmacologically active substances, for example with diuretics, antiarrhythmics, $\beta$-blockers, sedatives, cardiac vasodilators, hypolipidemics and the like.

The active substances according to the invention can be administered orally, parenterally (intramuscularly, intravenously, subcutaneously), rectally or as an aerosol or can be used locally.

The following doses are used on mammals, including humans:

To lower the blood pressure: daily dose: 0.1–200 mg; single dose: 0.1–25 mg.

The new compounds can be used either alone or mixed with pharmacologically tolerated vehicles. For a form for oral use, the active compounds are mixed with the substances customary for this purpose and converted by customary methods into suitable forms for administration, such as tablets, hard capsules, aqueous, alcoholic or oily suspensions or aqueous, alcoholic or oily solutions. Suitable inert vehicles which can be used are, for example, magnesium carbonate, lactose or corn starch with the addition of other substances, such as, for example, magnesium stearate. The formulation can be thereby carried out either as a dry or as a moist granular powder. Particularly suitable oily vehicles or solvents are vegetable and animal oils, such as, for example, sunflower oil or cod-liver oil.

An important form for use, for example, for emergency therapy comprises intravenous administration. For this purpose, the active compounds or their physiologically tolerated salts, where they have sufficient solubility, are brought to solution with the customary auxiliaries for this purpose, which, for example, can have solubilizing or buffering properties.

Physiologically tolerated salts are formed, for example, with the following acids: hydrochloric, hydrobromic or hydriodic acid, phosphoric acid, sulfuric acid, methyl sulfuric acid, amidosulfonic acid, nitric acid, tartaric acid, lactic acid, malonic acid, fumaric acid, oxalic acid, citric acid, malic acid, mucic acid, benzoic acid, salicylic acid, aceturic acid, pamoic acid, naphthalene-1,5-disulfonic acid, ascorbic acid, phenylacetic acid, p-aminosalicylic acid, hydroxyethanesulfonic acid, benzene-sulfonic acid or synthetic resins which contain acid groups, for example, those having ion exchange effects.

Examples of suitable solvents for intravenous administration are: water, physiological saline or dilute alcohols, such as, for example, ethanol, propanediol or glycerol, in addition, sugar solutions, such as, for example, glucose or mannitol solutions, or also a mixture of the various solvents mentioned.

The following examples illustrate the invention:

EXAMPLE 1

9,10-Dimethoxy-3,4,6,7-tetrahydro-2H-triazino(2,1-a)isoquinoline-2,4-dione

A suspension of 9.00 g of sodium hydride in 250 ml of dry benzene was treated with 40 g of 6,7-dimethoxy-1-imino-1,2,3,4-tetrahydroisoquinoline hydriodide and the mixture was heated under reflux for 3 hours. After the addition of 30.0 ml of ethoxycarbonyl isocyanate in 200 ml of benzene, the mixture obtained was heated under reflux for 16 hours. The excess sodium hydride was destroyed with methanol and the reaction mixture was diluted with 500 ml of water. The aqueous phase was separated off and acidified with dilute hydrochloric acid which produced a solid material which was filtered, washed with water, dried and recrystallized from methanol.

Yield: 26.0 g. Melting point: 292°–293° C.

EXAMPLE 2

General process for the preparation of the compounds of the formula I from compounds of the formula Ia A mixture of a compound of the formula Ia with phosphorus oxytrichloride (10–20 mole) is heated under reflux for 3 hours. The excess phosphorus oxytrichloride is then distilled off under reduced pressure and the residue is heated with an appropriate amine of the formula

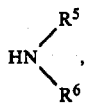

employed in excess (5-10 mole), in the presence of a base, preferably the amine employed in excess as the reagent or of an acid acceptor and preferably in the presence of an appropriate solvent as listed above. The reaction mixture can be heated at the reflux temperature for 2 to 20 hours. The residue obtained after evaporation of the solvent under reduced pressure is treated with water then extracted with an organic solvent. The extract obtained can then appropriately be washed, allowed to stand over anhydrous sodium sulfate and evaporated to dryness. The residue thus obtained can be purified by chromatography and recrystallized to give the desired compound, it being possible for the latter to be optionally converted into its acid addition salt.

EXAMPLE 3

9,10-Dimethoxy-2-tert.-butylamino-6,7-dihydro-4H-triazino(2,1-a)isoquinolin-4-one hydrochloride A mixture of 1.0 g of 9,10-dimethoxy-3,4,6,7-tetrahydro-2H-triazino(2,1-a)isoquinoline-2,4-dione and 10 ml of phosphorus oxytrichloride was heated under reflux for 3 hours and excess phosphorus oxytrichloride was distilled off under reduced pressure.

The residue was then dissolved in 30 ml of chloroform, treated with 5 ml of tertiary butylamine and heated under reflux for 20 hours. Excess amine was distilled off under reduced pressure. The residue was extracted with chloroform. The extract obtained was washed consecutively with 10% strength sodium hydroxide and water, dried over anhydrous sodium sulfate and evaporated under reduced pressure. The residue obtained was converted by reaction with etherial hydrochloric acid in ethanol into its hydrochloride, which was then recrystallized from methanol/water. Yield: 0.8 g. Melting point: 243°-245° C.

EXAMPLE 4

9,10-Dimethoxy-2-(2,4-dichloroanilino)-6,7-dihydro-4H-triazino(2,1-a)isoquinolin-4-one hydrochloride The process was carried out substantially as described under Example 3, but using 2,4-dichloroaniline instead of tert.-butylamine. Before conversion into its hydrochloride, the product of the process was purified by passing over a silica gel column with chloroform as the eluent. Yield of hydrochloride: 47%. Melting point: 222°-224° C.

EXAMPLE 5

9,10-Dimethoxy-2-mesitylamino-6,7-dihydro-4H-triazino(2,1-a)isoquinolin-4-one hydrochloride The process was carried out substantially as described under Example 3, but using mesitylamine instead of tert.-butylamine. Yield of hydrochloride: 55%. Melting point: 240°-242° C.

EXAMPLE 6

9,10-Dimethoxy-2-morpholino-6,7-dihydro-4H-triazino(2,1-a)isoquinolin-4-one hydrochloride The process was carried out substantially as described under Example 3, but using morpholine instead of tert.-butylamine. Yield of hydrochloride: 73%. Melting point: 252°-253° C.

EXAMPLE 7

9,10-Dimethoxy-2-mesitylamino-6,7-dihydro-2H-triazino(2,1-a)isoquinoline-4-thione A mixture of 14.0 g of 9,10-dimethoxy-2-mesitylamino-6,7-dihydro-4H-triazino(2,1-a)isoquinolin-4-one and 12.0 g of 2,4-bis-(4-methoxyphenyl)-1,3,2,4-dithiadiphosphetane-2,4-disulfide in 350 ml of dioxane was heated to 95°-100° C. for 16 hours, excess solvent was allowed to evaporate off under reduced pressure and the residue was treated with water and extracted with chloroform.

The extract was washed consecutively with 10% strength sodium hydroxide and with water, the organic layer was left to stand over anhydrous sodium sulfate and evaporated to dryness. The residue obtained was purified by passing over a silica gel column using chloroform as the eluent. After evaporation of the solvent, the corresponding 4-thione was obtained. Yield: 10.0 g. Melting point 253°-254° C.

EXAMPLE 8

9,10-Dimethoxy-2-mesitylimino-4-ethylthio-6,7-dihydro-2H-triazino(2,1-a)isoquinoline hydriodide A solution of 10.0 g of 9,10-dimethoxy-2-mesitylamino-6,7-dihydro-4H-triazino(2,1-a)isoquinoline-4-thione in 300 ml of tetrahydrofuran prepared as in Example 7 was treated with 25 ml of ethyl iodide and the reaction mixture obtained was heated for 2 hours. The solid material obtained was filtered, 9,10-dimethoxy-2-mesitylimino-4-ethylthio-6,7-dihydro-2H-triazino(2,1-a)isoquinoline hydriodide resulting in a yield of 11.50 g. Melting point: 208°-211° C.

EXAMPLE 9

9,10-Dimethoxy-2-mesitylimino-4-(4-methylanilino)-6,7-dihydro-2H-triazino(2,1-a)isoquinoline hydriodide A mixture of 2.5 g of the compound obtained in Example 8 and 2.5 g of 4-methylaniline was heated at 100° C. for 4 hours. The reaction product obtained was cooled down and triturated with excess diethyl ether, a solid material resulting which was filtered and purified by recrystallization from methanol/diethyl ether. Yield: 1.8 g. Melting point: 258°-260° C.

EXAMPLE 10

9,10-Dimethoxy-2-mesitylimino-4-amino-6,7-dihydro-2H-triazino(2,1-a)isoquinoline monohydrate 2.5 g of the compound obtained in Example 8 were treated with 25 ml of a saturated solution of ammonia in ethanol and the solution obtained was stirred at room temperature for 2 hours. The solution was largely concentrated in vacuo and diluted with diethyl ether, a solid material being obtained which was recrystallized from a mixture of methanol and ether. Yield: 2.0 g. Melting point 261°-263° C.

EXAMPLE 11

9,10-Dimethoxy-2-mesitylimino-4-(2,4-dimethylanilino)-6,7-dihydro-2H-triazino(2,1-a)isoquinoline hydriodide A mixture of 2.0 g of the compound obtained in Example 8 to 5 ml of 2,4-dimethylaniline was heated at 100° C. for 4 hours. The mixture obtained was cooled down and triturated with diethyl ether, a solid material resulting which was purified by recrystallization from a mixture of methanol and diethyl ether. Yield: 1.7 g. Melting point: 252°-255° C.

We claim:

1. A compound of the formula

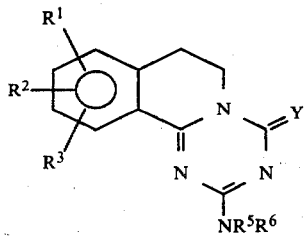

or an acid addition salt thereof, wherein
$R^1$, $R^2$, and $R^3$, taken alone, are the same or different and are hydrogen, lower alkoxy, acyloxy, or halogen, or wherein an adjacent pair of $R^1$, $R^2$, and $R^3$, taken together, are alkylenedioxy;
$R^5$, and $R^6$, taken alone, are the same or different and are hydrogen, lower alkoxy, amino, lower alkylamino, lower dialkylamino, acylamino, lower alkoxycarbonylamino, a nitrogen-containing heterocycle, lower alkyl, $C_3$-$C_6$-cycloalkl, lower dialkylaminoalkyl, aralkyl, phenyl, or phenyl mono- to tri-substituted by halogen, hydroxy, nitro, $C_1$-$C_3$-alkyoxy, or $C_1$-$C_3$-alkyl, or wherein $R^5$ and $R^6$, taken together with the nitrogen atom to which they are bonded, are a substituted or unsubstituted nitrogen heterocycle or such a heterocycle containing a further nitrogen or oxygen atom; and
Y is oxygen or sulfur.

2. A compound or salt as in claim 1 wherein $R^1$, or $R^2$, or both is $C_1$-$C_3$-alkoxy and $R^3$ is hydrogen, and wherein $R^5$ and $R^6$ are taken alone and are hydrogen, a nitrogen containing heterocycle, $C_1$-$C_6$-alkyl, phenyl, or phenyl mono- to tri-substituted by halogen, hydroxy, nitro, $C_1$-$C_3$-alkyoxy, or $C_1$-$C_3$-alkyl, or wherein $R^5$ and $R^6$ are taken together.

3. A compound or salt as in claim 1 wherein Y is oxygen, one or $R^5$ or $R^6$, taken alone, is hydrogen and the other is hydrogen, $C_1$-$C_6$-alkyl, piperidino, or is phenyl mono-, di-, or tri-substituted by halogen, $C_1$-$C_3$-alkyl, or $C_1$-$C_3$-alkoxy, or wherein $R^5$ and $R^6$, taken together with the nitrogen atom to which they are bonded, are unsubstituted or substituted pyrrolidino, piperazino, or morpholino.

4. A compound or salt as in claim 2 wherein Y is oxygen, one or $R^5$ or $R^6$ taken alone, is hydrogen and the other is hydrogen, $C_1$-$C_6$-alkyl, piperidino, or is phenyl, mono-, di-, or tri-substituted by halogen, $C_1$-$C_3$-alkyl, or $C_1$-$C_3$-alkoxy, or wherein $R^5$ and $R^6$, taken together with the nitrogen atom to which they are bonded, are unsubstituted or substituted pyrrolidino, piperazino, or morpholino.

5. A compound or salt as in claim 1 wherein said alkylenedioxy is methylendioxy or ethylenedioxy.

6. A compound as in claim 1 which is 9-10-dimethoxy-2-mesitylamino-6,7-dihydro-4H-triazino(2,1-a)isoquinolin-4-one hydrochloride.

7. 9,10-Dimethoxy-2-tert.-butylamino-6,7-dihydro-4H-triazino(2,1-a)isoquinolin-4-one hydrochloride.

8. 9,10-Dimethoxy-2-(2,4-dichloroanilino)-6,7-dihydro-4H-triazino(2,1-a)isoquinolin-4-one hydrochloride.

9. 9,10-Dimethoxy-2-mesitylamino-6,7-dihydro-4H-triazino(2,1-a)isoquinolin-4-one hydrochloride monohydrate.

10. 9,10-Dimethoxy-2-morpholino-6,7-dihydro-4H-triazino(2,1-a)isoquinolin-4-one hydrochloride.

11. A pharmaceutical composition for the treatment of hypertension, which composition comprises a hypotensively effective amount of a compound or salt as in claim 1 and a pharmaceutically acceptable carrier therefor.

12. A method for treating hypertension in a patient suffering therefrom, which method comprises administering to said patient a hypotensively effective amount of a compound as in claim 1.

* * * * *